United States Patent [19]
Gross

[11] Patent Number: 5,824,066
[45] Date of Patent: Oct. 20, 1998

[54] ANNULOPLASTY PROSTHESIS

[75] Inventor: Jeffrey M. Gross, Mission Viejo, Calif.

[73] Assignee: Medtronic, Inc., Minneapolis, Minn.

[21] Appl. No.: 861,245

[22] Filed: May 21, 1997

Related U.S. Application Data

[63] Continuation of Ser. No. 565,134, Dec. 1, 1995, abandoned.
[51] Int. Cl.⁶ ........................................................ A61F 2/24
[52] U.S. Cl. .................................................................. 623/2
[58] Field of Search ........................................ 623/2, 900

[56] References Cited

U.S. PATENT DOCUMENTS

| | | |
|---|---|---|
| 3,656,185 | 4/1972 | Carpentier . |
| 4,042,979 | 8/1977 | Angell . |
| 4,290,151 | 9/1981 | Massana . |
| 4,489,446 | 12/1984 | Reed . |
| 4,602,911 | 7/1986 | Ahmadi et al. ............................. 623/2 |
| 4,917,698 | 4/1990 | Carpentier et al. ........................ 623/2 |
| 5,061,277 | 10/1991 | Carpentier . |
| 5,064,431 | 11/1991 | Gilbertson . |
| 5,104,407 | 4/1992 | Lam . |
| 5,163,953 | 11/1992 | Vince ........................................ 623/2 |
| 5,201,880 | 4/1993 | Wright et al. ............................. 623/2 |
| 5,290,300 | 3/1994 | Cosgrove et al. ...................... 606/148 |
| 5,306,296 | 4/1994 | Wright et al. ............................. 623/2 |
| 5,593,424 | 1/1997 | Northrup ............................... 606/232 |
| 5,593,435 | 1/1997 | Carpentier et al. ........................ 623/2 |

FOREIGN PATENT DOCUMENTS

| | | | |
|---|---|---|---|
| 1205905 | 1/1986 | U.S.S.R. .................................... 623/2 |
| 9407437 | 4/1994 | WIPO ....................................... 623/2 |

OTHER PUBLICATIONS

Bashour YTT. et al. Reparative Operations for Mitral Valve Incompetence: An Emerging Treatment of Choice. (American Heart Journal 1987;113(5):1199–1206).
Carpentier A. Cardiac Valve Surgery –The "French Correction." (J Thorac Cardiovasc Surg 1983;86:323–337.
Cohen LH. Mitral Valve Surgery: Replacement vs. Reconstruction. (Hospital Practice Aug., 1991; 26(8):49–58).
Cosgrove DM Surgery for Degenerative Mitral Valve Disease. (seminars in Thorac and Cardiovasc surg 1989: 1(2):183–93.).
David TE, et al. Mitral Valve Annuloplasty: The Effect of the Type on Left Ventricular Function. (Ann of Thorac Surg 1989; 47:524–28.).
Duran CMG, et al. Clinical and Hemodynamic Performance of a Totally Flexible Prosthetic Ring for Atrioventricular alve Reconstruction. (Ann of Thorac Surg 1976;22(5):458–63).
Duran CMG, Repair of Anterior Mitral Leaflet Chordal Rupture of Elongation (The Flip–Over Technique.) (J of Card Surg 1986;1(2):161–66.).
Galloway AC, et al. A Comparison of Mitral Valve Replacement: Intermediate–Term Results, (Ann of Thorac Surg 1989;47:655–62.).
Loop FD. Long–Term Results of Mitral Valve Repair. (Seminars in Thorac and Cardiovasc Surg 1989;1(2):203–10.).
Oury JH, et al. Mitral Valve Reconstruction for Mitral Regurgitation (J Card Surg 1986;1(3.):217–231.
Sand ME, et al. A Comparison of Repair and Replacement for Mitral Valve (J Thorac Cardiovasc Surg 1987;94 (2):208–19.).
Tunnick PA, et al. and Association Between Residual Mitral Regurgitation and Left Ventricular Outflow Obstruction After Carpentier Ring Mitral Annuloplasty. (The American Journal of Cardiology; 70:689–691, 1992.).
Cohen DJ, et la. Systollic Anterior Motion of the Chordal Apparatus After Ring Insertion. (American Heart Journal; 124(3): 666–670, 1992).
DSalati M, et al. Posterior Pericardial Annuloplasty: A Physiological Correction. (Eur.J.Cardio–thorac Surg; 5:226–229,1991.).

*Primary Examiner*—David H. Willse
*Attorney, Agent, or Firm*—Harold R. Patton; Curtis D. Kinghorn; Peter Forrest

[57] ABSTRACT

An annuloplasty ring having an adjustable configuration. The ring takes the form of a tubular sleeve surrounding frame members which be deflected by means of drawstrings.

45 Claims, 2 Drawing Sheets

ANNULOPLASTY PROSTHESIS

CROSS-REFERENCE TO RELATED APPLICATION

This application is a continuation of application Ser. No. 08/565,134, filed Dec. 1, 1995, now abandoned.

BACKGROUND OF THE INVENTION

The present invention pertains generally to annuloplasty rings and more specifically to adjustable annuloplasty rings.

Annuloplasty prostheses, generally known as annuloplasty rings, are employed in conjunction with valvular reconstructive surgery to assist in the correction of heart valve defects such as stenosis and valvular insufficiency. Rings for use in repair of both mitral and tricuspid valves are widely known. Early annuloplasty ring designs, and most commercially available annuloplasty rings are fixed in circumference, and thus must be made available in a variety of sizes so that they may be used with valves of differing sizes. However, a number of patents propose annuloplasty rings having adjustable circumferences, including U.S. Pat. No. 4,042,979, issued to Angell, U.S. Pat. No. 4,290,151, issued to Massana and U.S. Pat. No. 5,064,431, issued to Gilbertson et al.

While some ring designs are very flexible throughout their circumference, such as the Duran annuloplasty ring, manufactured and sold by Medtronic, alternative designs employ more rigid frames which completely or partially surround the ring. Rigid or partially rigid annuloplasty rings are disclosed in U.S. Pat. No. 3,656,185, U.S. Pat. No. 5,061,277 and in U.S. Pat. No. 5,104,407.

SUMMARY OF THE INVENTION

The present invention provides an annuloplasty ring which may be reconfigured after installation around the valve annulus. Unlike the adjustable annuloplasty rings described above, which are adjustable only to vary the lengths of designated portions of the circumstance, the present ring may be adjusted to vary the curvature of the prosthesis, allowing for wide flexibility in adjusting the configuration of the valve annulus to assure proper valve function.

The present employs internal frame members to control the curvature of segments of the ring. The curvature of the frame members is adjustable by means of drawstrings which are employed to vary the curvature along one or more portions of the frame members. In the preferred embodiment, two spaced, curved, frame members are employed, each employing multiple drawstrings to provide for a high degree of control of curvature. The first frame member extends from the antero-lateral trigone, partially around the posterior leaflet. No frame is provided between the antero-lateral trigone and the postero-medial trigone along the anterior portion of the mitral annulus. The second frame member extends from the postero-medial trigone partially around the posterior leaflet, but spaced from the first frame member. No frame is provided along the posterior segment of the mitral annulus, between the ends of the first and second frame members. The annulus is thus free to move normally in the regions between the frame members, but is prevented from undergoing systolic anterior motion in the regions adjacent the frame members.

In the disclosed embodiment, the annuloplasty ring is provided with a temporary metal spacer extending between the two ends of the prosthesis, in order to simplify installation. After installation, the spacer is removed.

DETAILED DESCRIPTION OF THE PREFERRED EMBODIMENTS

Figure 1:
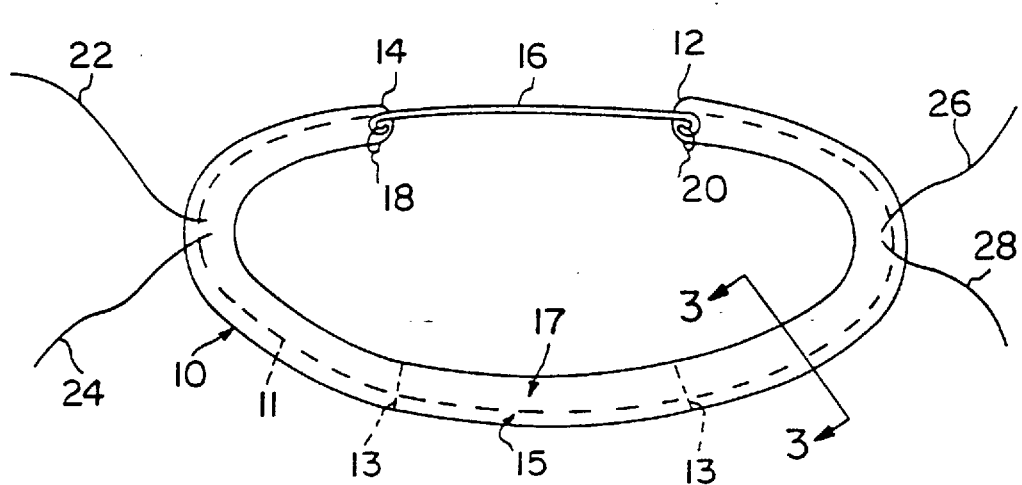
FIG. 1 is a plan view of the invention, configured in the form of a mitral annuloplasty ring.
Figure 3:
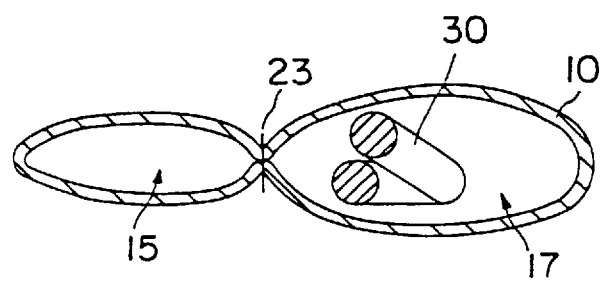
FIG. 3 is a cross section through the annuloplasty ring illustrated in FIG. 1.

FIG. 1 illustrates a mitral annuloplasty ring according to the present invention. Externally, the ring is covered with a ribbed tubular dacron cloth sleeve 10, of moderate porosity. The ribbing of the tubular dacron sleeve 10 allows it to follow the curvature of the prosthesis without kinking of the fabric. The cross section of the tubular dacron sleeve 10 is formed into two elliptical channels by means of a longitudinal ultrasonic weld, sutures, adhesive or the like, as illustrated in FIG. 3. Inner channel 17 is located adjacent the inner, concave edge of the ring and outer channel 15 is located adjacent the outer, convex edge of the ring. Externally, a thread 11 of a different color from the surrounding dacron is used to mark the division between the inner channel 17 and the outer channel 15. Additionally, threads 13 of a different color than the surrounding dacron are placed radially in two locations to denote the ends of the internal frame members, adjacent the posterior valve annulus. Suturing to the annulus is permitted along the exterior channel 15 and along the interior channel 17 between the two radial markers 13. The sleeve is sealed at ends 12 and 14 by means of ultrasonic welds, sutures or adhesive. As implanted, the first end 12 is adapted to located adjacent the postero-medial trigone and the second end 14 is adapted to be located adjacent the antero-lateral trigone, with the prosthesis generally extending around the posterior leaflet.

A spacer 16 is sutured to the ends 12 and 14 of the prosthesis by means of sutures 18 and 20. Spacer 16 aids in maintaining the prosthesis in an appropriate configuration during shipment and during implantation, and provides an appropriate frame of reference to assist in proper location of ends 12 and 14 relative to the valve annulus. The spacer may be fabricated of MP35N alloy, or other similar inert biocompatible metal and is removed after the ring is secured in place to the valve annulus. Extending from the top of each side of the inner channel 17 are drawstrings 22, 24, 26 and 28 which serve to adjust the curvature of the prosthesis, as described below.

Figure 2:
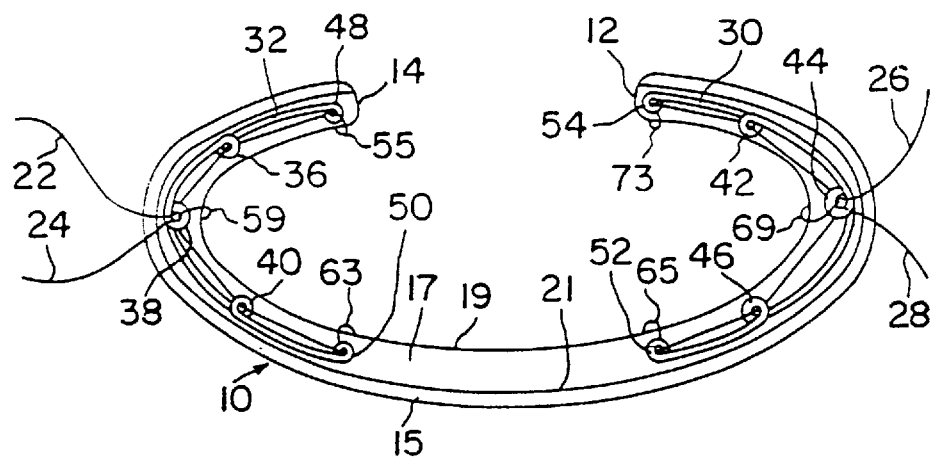
FIG. 2 illustrates the functioning and relationship of the adjustable frame members, within the annuloplasty ring illustrated in FIG. 1.

FIG. 2 illustrates the internal structure of the ring. In this view, the outline of the dacron sleeve 10 is indicated at 19, with the division between inner channel 17 and outer channel 15 indicated by line 21. Mounted within the sleeve 10 are frame members 30 and 32. The frame members 30 and 32 are manufactured of MP35N alloy or other biocompatible metal wire, and extend from the ends (12 and 14) of the prosthesis, around the prosthesis, to two points adjacent the central portion of prosthesis, which at implant will be adjacent the posterior leaflet. The ends of the frame members are spaced from one another within sleeve 10, so that the valve annulus may assume its normal configuration during opening and closing of the valves in this region intermediate frame members 30 and 32.

Each of the two frames 30 and 32 are wound to define loops 36, 38, 40, 42, 44 and 46, spaced along the length of the frame members 30 and 32. The ends of the frame members are wound to define loops 48, 50, 52 and 54 which may serve as anchor points for location of drawstrings and may serve as loops through which drawstrings pass. Similarly, each of the loops 36, 38, 40, 42, 44 and 46 may also serve as anchoring points for drawstrings and/or as loops through which a drawstring may pass. Loops 38, 44, 48, 50, 52 and 54 are sutured to the tubular dacron sleeve, as illustrated at 59, 69, 55, 63, 65 and 73. These sutures maintain the frame members 30 and 32 at their proper locations within the inner channel 17 of tubular sleeve 10.

As illustrated, each of the two frame members is provided with a pair of drawstrings 22, 24, 26 and 28. For frame member 32, drawstrings 22 and 24 both enter through the central loop 38, and extend through intermediate loops 36 and 40 to opposite ends of the frame member where they are anchored at end loops 48 and 50, respectively. Tension applied to drawstring 22 thus causes deflection of frame member 32 between loops 38 and 48 in a way similar to the way a fishing pole bends when a fish is hooked. Similarly, tension applied to draw string 24 causes deflection of the frame member 32 between loops 38 and 50. Drawstrings 26 and 28 are routed and function in an equivalent fashion with regard to frame member 30. Drawstrings 22, 24, 26 and 28 may be prolene type sutures, preferably coated with Teflon or other low friction material.

During implantation, the ring is mounted around the mitral valve annulus in a conventional fashion, with sutures appropriately spaced and located to provide any necessary reduction in overall annulus circumference. This much of the implant procedure corresponds to the procedures used to implant prior art nonadjustable prostheses such as the Duran annuloplasty ring manufactured and sold by Medtronic or the Carpentier annuloplasty rings sold by Baxter International, Inc. Following suturing of the ring to the valve annulus, the spacer 16 is removed by trimming of sutures 18 and 20 (FIG. 1), and the curvature of the ring is adjusted by applying tension to appropriate ones of drawstrings 22, 24, 26 and 28 to assure proper annulus configuration and coaption of the valve leaflets. After the prosthesis has assumed an appropriate curvature, the drawstrings are tied at their point of exit from the annuloplasty ring, so that the desired configuration will be maintained.

FIG. 3 illustrates a cross section through the ring as illustrated in FIG. 1. In this view the elliptical configurations of inner channel 17 and outer channel 15 are visible. Also illustrated are threads 23, which are employed to create the division between the inner and outer channels. Frame member 30 is visible in cross section.

Figure 4:
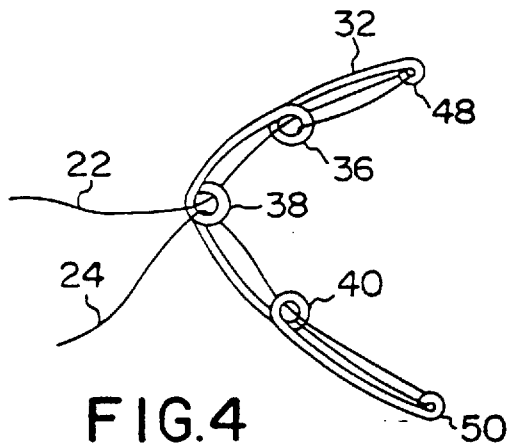
FIGS. 4, 5, 6 and 7 illustrate alternative mechanisms for adjusting the curvature of the frame members illustrated in FIG. 2.

FIG. 4 illustrates an alternative mechanism for stringing the drawstrings with respect to the frame members. Only frame member 32 is illustrated, however, it is to be understood that the same or a different stringing pattern for the drawstrings may be employed on the second frame member which would accompany frame member 32 in the prosthesis. The same is true of FIGS. 5–7 which also illustrate alternative relationships between frame member 30 or frame member 32 and the drawstrings.

In FIG. 4, drawstrings 22 and 24 both enter the central loop 38, preceding to end loops 48 and 50, passing through loops 36 and 40, respectively, as illustrated in FIG. 2. However, rather than being anchored to loops 48 and 50, the drawstrings proceed through the loops back to intermediate loops 36 and 40, where they are anchored.

Figure 5:
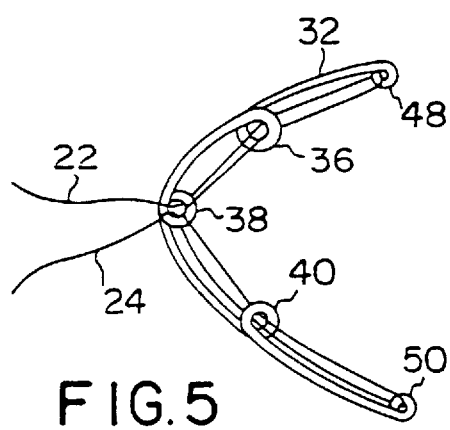

FIG. 5 corresponds to FIG. 4 with the exception that in the case of FIG. 4, drawstrings 22 and 24 are routed through intermediate loops 36 and 40 and are anchored at central loop 38. The drawstring configurations of FIGS. 4 and 5 provide an improved mechanical ratio as compared to the drawstring configuration in FIG. 2, with the result that a greater extension of the drawstring is required to effect a predetermined curvature in the frame member 32.

Figure 6:
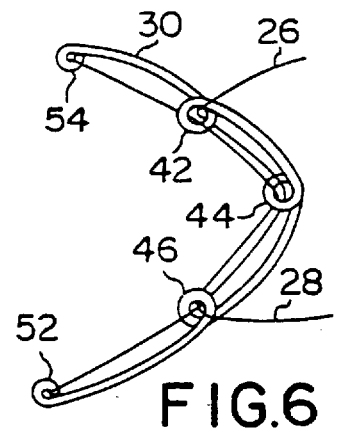
Figure 7:
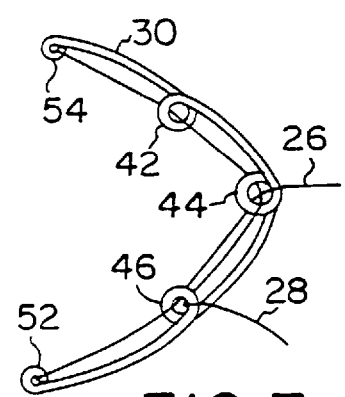

FIG. 6 and FIG. 7 illustrate alternative drawstring configurations directed toward providing enhanced ability to deflect the frame around the central loop. In FIG. 6, drawstrings 26 and 28 enter the prosthesis through intermediate loops 42 and 46, respectively, passing through central loop 44, and then extending through loops 42 and 46 to end loops 52 and 54, to which the drawstrings are anchored. Tension applied to drawstring 26 thus causes the prosthesis to flex between loops 42 and 52. Similarly, tension applied to drawstring 28 causes the frame member 30 to flex between loops 46 and 54.

FIG. 7 illustrates a drawstring configuration which is a hybrid of those illustrated in FIGS. 2 and 6, with drawstring 26 routed corresponding to drawstring 26 in FIG. 2 and drawstring 28 routed as in FIG. 6.

As can be seen, a wide variety of drawstring configurations are available, with variations in drawstring configuration readily employed to determine the location and amount of flexing of the frame members induced by tension on the drawstrings. Similarly, it should be understood frame members having greater or fewer numbers of loops, of greater or lesser diameters, are also within the scope of the present invention. It is believed that as prosthesis of this general type are further developed, specific frame configurations and drawstring configurations may be developed which are particularly optimized for correction of particular types of mitral valve defects.

In the disclosed embodiment, two independent frame members are provided, spaced from one another within the inner channel of the sleeve. However, a single frame member extending around the circumference of the prosthesis, whether configured as an open or closed curve might also be substituted for some applications.

While the present invention is disclosed as a prosthesis having fixed length, the adjustable frame members of the present invention may also be incorporated in prosthesis having adjustable lengths. In such cases, it is to be expected that adjustment of the overall length of the prosthesis would be accomplished by a set of one or more drawstrings employed to lengthen or shorten the spacing between the frames. Similarly, while the disclosed embodiment takes the form of a mitral annuloplasty prosthesis, it is believed that the basic mechanism for adjustment of the curvature of the frame members may be of value in other applications, including other valve annuloplasty prostheses as well as prostheses designed to correct other deformations of annular or tubular structures within the body.

As such, the above disclosures should be taken as exemplary, rather than limiting with regard to the claims that follow. In conjunction with the above application,

I claim:

1. A mitral annuloplasty prosthesis comprising:

a fabric sheath;

first and second frame members mounted within the sheath and spaced from one another, the frame members configured such that after implant, the first frame member extends from the antero-lateral trigone to a first point adjacent the posterior leaflet and the second frame member extends from the postero-medial trigone to a second point adjacent the posterior leaflet, the first and second points spaced from one another.

2. A mitral annuloplasty prosthesis according to claim 1 further comprising means for applying tension between two points on the frame members to cause deflection of the frame members.

3. A mitral annuloplasty prosthesis according to claim 2 wherein the means for applying tension comprise drawstrings.

4. A mitral annuloplasty prosthesis according to claim 3 wherein the frame members comprise metal wires.

5. A mitral annuloplasty prosthesis according to claim 4 wherein the metal wires are wound to define loops.

6. A mitral annuloplasty prosthesis according to claim 5 wherein the drawstrings are affixed to the frame members and pass through the loops.

7. A mitral annuloplasty prosthesis according to claim 1 wherein the fabric comprises a tubular sleeve, divided into two internal channels and wherein the first and second frame members are located within one of the channels.

8. A mitral annuloplasty prosthesis according to claim 7 wherein the prosthesis follows a curve and has an inner, concave edge and an outer, convex edge, and wherein the one of the channels is adjacent the inner edge.

9. A mitral annuloplasty prosthesis comprising:
   a fabric sheath;
   a first frame member mounted within the sheath, the first frame member having a first end and a second end, the prosthesis being configured such that after implant, the first frame member extends from the antero-lateral trigone to a first point adjacent the posterior leaflet, the first frame member having a first central loop centrally located along the first frame member and a first end loop located at the first end of the first frame member; and,
   a first drawstring, the first drawstring passing through the first central loop and the first end loop and being anchored along the first frame member.

10. The mitral annuloplasty prosthesis of claim 9 wherein the first drawstring is anchored to the first central loop.

11. The mitral annuloplasty prosthesis of claim 9 further comprising:
    a second end loop located at the second end of the first frame member; and,
    a second drawstring, the second drawstring passing through the first central loop and the second end loop and being anchored along the first frame member.

12. The mitral annuloplasty prosthesis of claim 11 wherein the second drawstring is anchored to the first central loop.

13. The mitral annuloplasty prosthesis of claim 9 further comprising:
    a first intermediate loop located on the first frame member between the first central loop and the first end loop;
    wherein, the first drawstring passes through the first central loop, the first intermediate loop and the first end loop and is anchored along the first frame member.

14. The mitral annuloplasty prosthesis of claim 13 wherein the first drawstring is anchored to the first central loop.

15. The mitral annuloplasty prosthesis of claim 13 wherein the first drawstring is anchored to the first intermediate loop.

16. The mitral annuloplasty prosthesis of claim 13 further comprising:
    a second end loop located at the second end of the first frame member; and,
    a second drawstring, the second drawstring passing through the first central loop and the second end loop and being anchored along the first frame member.

17. The mitral annuloplasty prosthesis of claim 16 wherein the second drawstring is anchored to the first central loop.

18. The mitral annuloplasty prosthesis of claim 16 further comprising:
    a second intermediate loop located on the first frame member between the first central loop and the second end loop;
    wherein, the second drawstring passes through the first central loop, the second intermediate loop and the second end loop and is anchored along the first frame member.

19. The mitral annuloplasty prosthesis of claim 16 wherein the second drawstring is anchored to the first central loop.

20. The mitral annuloplasty prosthesis of claim 16 wherein the second drawstring is anchored to the second intermediate loop.

21. The mitral annuloplasty prosthesis of claim 9 further comprising:
    a second frame member mounted within the sheath and spaced from the first frame member, the second frame member having a first end and a second end, the second frame member configured such that after implant, the second frame member extends from the postero-medial trigone to a second point adjacent the posterior leaflet, the second frame member having a second central loop centrally located along the second frame member and a third end loop located at the first end of the second frame member; and,
    a third drawstring, the third drawstring passing through the second central loop and the third end loop and being anchored along the second frame member.

22. The mitral annuloplasty prosthesis of claim 21 wherein the third drawstring is anchored to the second central loop.

23. The mitral annuloplasty prosthesis of claim 21 further comprising:
    a fourth end loop located at the second end of the second frame member; and,
    a fourth drawstring, the fourth drawstring passing through the second central loop and the fourth end loop and being anchored along the second frame member.

24. The mitral annuloplasty prosthesis of claim 23 wherein the fourth drawstring is anchored to the second central loop.

25. The mitral annuloplasty prosthesis of claim 21 further comprising:
    a third intermediate loop located on the second frame member between the second central loop and the third end loop;
    wherein, the third drawstring passes through the second central loop, the third intermediate loop and the third end loop and is anchored along the second frame member.

26. The mitral annuloplasty prosthesis of claim 25 wherein the third drawstring is anchored to the second central loop.

27. The mitral annuloplasty prosthesis of claim 25 wherein the third drawstring is anchored to the third intermediate loop.

28. The mitral annuloplasty prosthesis of claim 25 further comprising:
   a fourth end loop located at the second end of the second frame member; and,
   a fourth drawstring, the fourth drawstring passing through the second central loop and the fourth end loop and being anchored along the second frame member.

29. The mitral annuloplasty prosthesis of claim 28 further comprising:
   a fourth intermediate loop located on the second frame member between the second central loop and the fourth end loop;
   wherein, the fourth drawstring passes through the second central loop, the fourth intermediate loop and the fourth end loop and is anchored along the second frame member.

30. The mitral annuloplasty prosthesis of claim 29 wherein the fourth drawstring is anchored to the second central loop.

31. The mitral annuloplasty prosthesis of claim 29 wherein the fourth drawstring is anchored to the fourth intermediate loop.

32. A mitral annuloplasty prosthesis comprising:
   a fabric sheath;
   a first frame member mounted within the sheath, the first frame member having a first end and a second end, the prosthesis being configured such that after implant, the first frame member extends from the antero-lateral trigone to a first point adjacent the posterior leaflet, the first frame member having a first central loop centrally located along the first frame member and a first end loop located at the first end of the first frame member; and,
   a first intermediate loop located on the first frame member between the first central loop and the first end loop;
   a first drawstring, the first drawstring passing through the first intermediate loop, the first central loop, back through the first intermediate loop and being anchored along the first frame member.

33. The mitral annuloplasty prosthesis of claim 32 wherein the first drawstring is anchored to the first end loop.

34. The mitral annuloplasty prosthesis of claim 32 further comprising:
   a second end loop located at the second end of the first frame member;
   a second intermediate loop located on the first frame member between the first central loop and the second end loop; and,
   a second drawstring, the second drawstring passing through the second intermediate loop, the first central loop, back through the second intermediate loop and being anchored along the first frame member.

35. The mitral annuloplasty prosthesis of claim 34 wherein the second drawstring is anchored to the second end loop.

36. The mitral annuloplasty prosthesis of claim 32 further comprising:
   a second frame member mounted within the sheath and spaced from the first frame member, the second frame member having a first end and a second end, the second frame member configured such that after implant, the second frame member extends from the postero-medial trigone to a second point adjacent the posterior leaflet, the second frame member having a second central loop centrally located along the second frame member and a third end loop located at the first end of the second frame member; and,
   a third intermediate loop located on the second frame member between the second central loop and the third end loop;
   a third drawstring, the third drawstring passing through the third intermediate loop, the second central loop, back through the third intermediate loop and being anchored along the second frame member.

37. The mitral annuloplasty prosthesis of claim 36 wherein the third drawstring is anchored to the third end loop.

38. The mitral annuloplasty prosthesis of claim 36 further comprising:
   a fourth end loop located at the second end of the second frame member;
   a fourth intermediate loop located on the second frame member between the second central loop and the fourth end loop; and,
   a fourth drawstring, the fourth drawstring passing through the fourth intermediate loop, the second central loop, back through the fourth intermediate loop and being anchored along the second frame member.

39. The mitral annuloplasty prosthesis of claim 38 wherein the fourth drawstring is anchored to the fourth end loop.

40. An annuloplasty prosthesis, comprising a frame member configured to extend from a trigone toward a posterior leaflet to a point proximally adjacent the posterior leaflet, a fabric covering at least a portion of the frame member, and a drawstring affixed to and cooperatively arranged with the frame member such that tension may be applied by the drawstring between two points on the frame member to deflect the frame member.

41. The annuloplasty prosthesis of claim 40 in which the frame member comprises a metal wire, wound to define a loop, and the drawstring is affixed to the metal wire and passes through the loop.

42. The annuloplasty prosthesis of claim 40 in which the fabric comprises a tubular sleeve, the frame member being located within the tubular sleeve.

43. The annuloplasty prosthesis of claim 42 in which the prosthesis follows a curve, has an inner concave edge and an outer convex edge, the tubular sleeve being adjacent the inner concave edge.

44. The annuloplasty prothesis of claim 40 in which the frame member is configured to extend from a postero-medial trigone to a point proximally adjacent the posterior leaflet.

45. The annuloplasty prothesis of claim 40 in which the frame member is configured to extend from a antero-medial trigone to a point proximally adjacent the posterior leaflet.

* * * * *